United States Patent [19]

Szablak et al.

[11] Patent Number: 4,531,437

[45] Date of Patent: Jul. 30, 1985

[54] ROTARY NEEDLE AND SYRINGE DESTRUCTOR

[75] Inventors: Michael J. Szablak, Stephens City; Glen E. Tomblin, Winchester, both of Va.

[73] Assignee: Rubbermaid Commercial Products Inc., Winchester, Va.

[21] Appl. No.: 544,622

[22] Filed: Oct. 24, 1983

[51] Int. Cl.³ .............................................. B26D 1/00
[52] U.S. Cl. ......................................... 83/165; 83/167; 83/199; 83/580; 83/925 R; 241/100
[58] Field of Search ................... 83/167, 925 R, 199, 83/200, 162, 165, 196, 580, 175, 176; 30/124; 241/99, 100; 414/407, 414; 220/260, 263

[56] References Cited

U.S. PATENT DOCUMENTS

| | | | |
|---|---|---|---|
| 3,404,593 | 10/1968 | Arcarese | 83/167 |
| 3,444,620 | 5/1969 | Ciampa | 30/231 |
| 3,469,750 | 9/1969 | Vanderbeck | 225/94 |
| 3,683,733 | 8/1972 | Johan | 83/199 |
| 3,785,233 | 1/1974 | Robinson | 83/167 |
| 3,851,555 | 12/1974 | Eldridge et al. | 83/165 |
| 4,035,911 | 7/1977 | Nethercutt et al. | 83/167 X |
| 4,255,996 | 3/1981 | Choksi | 83/140 |
| 4,275,628 | 6/1981 | Greenhouse | 83/580 |
| 4,404,881 | 9/1983 | Hanifl | 83/167 |

Primary Examiner—James M. Meister
Assistant Examiner—John L. Knoble
Attorney, Agent, or Firm—Renner, Kenner, Grieve & Bobak Co.

[57] ABSTRACT

A device for destructing needles and syringes includes a base housing (20) and an upper closure body (22). One side of the housing (20) is open to slidably receive a receptacle (21) to receive severed needles and associated parts. The body (22) includes a rotary die member (32,33) mounted therein for severing the needles and syringes. The receptacle (21) is automatically locked in a closed position upon withdrawal from the base housing (20).

11 Claims, 16 Drawing Figures

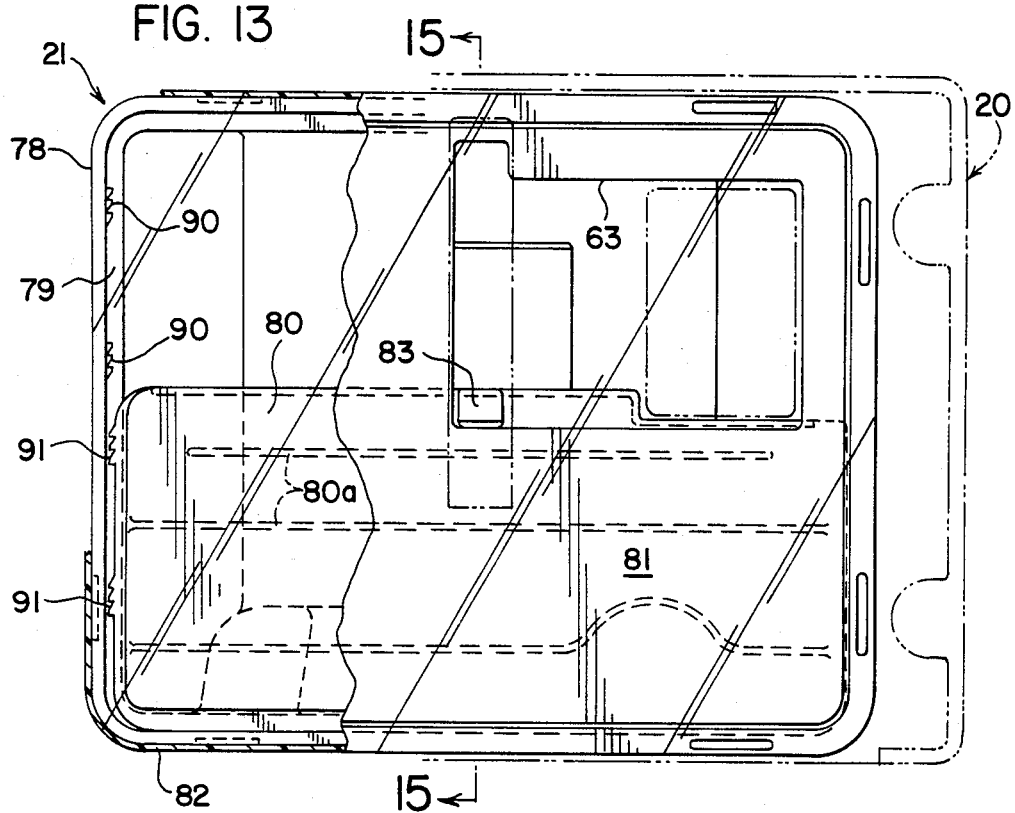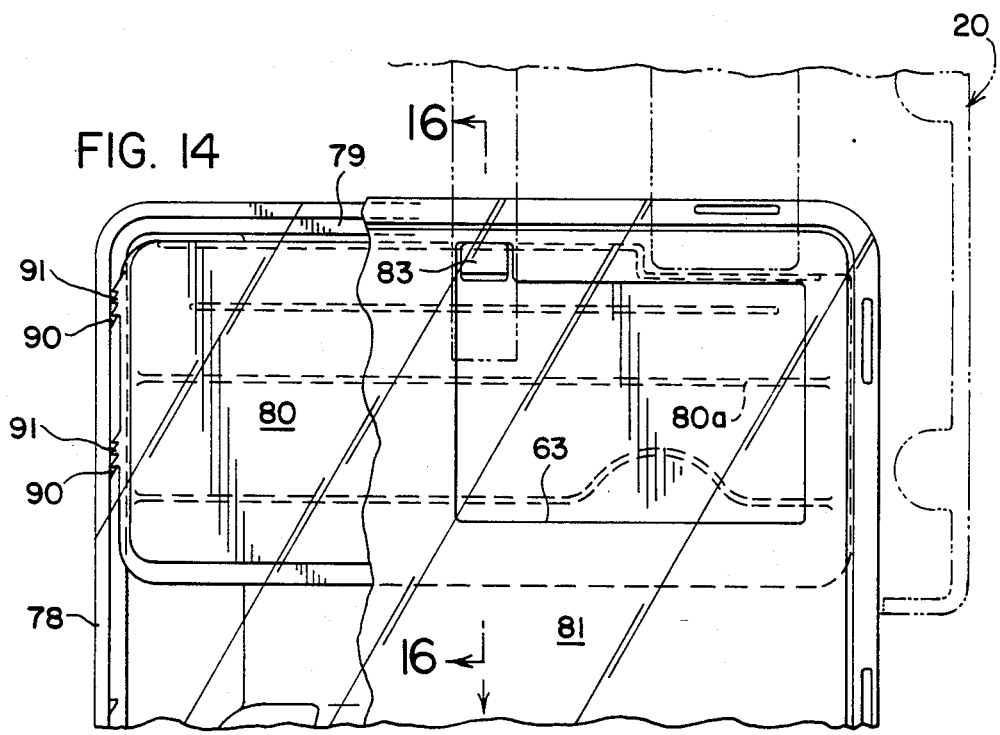

ROTARY NEEDLE AND SYRINGE DESTRUCTOR

TECHNICAL FIELD

The invention relates to devices for destroying or destructing hypodermic syringes and needles combined therewith so that they cannot be reused with resultant contamination, and for destroying the needles only in other needle and cartridge units.

BACKGROUND ART

U.S. Pat. No. 3,444,620 discloses a device for shearing the needle or cannula adjacent to the hub of an attached syringe by rotating a shearing member, having a cavity into which a syringe has been inserted, around a transversely disposed stationary shearing member having a connected cavity enclosing the cannula, whereby shearing edges at the connection of the cavities sever the cannula. However, there is no provision for severing or destroying any part of the syringe which may also be contaminated. Furthermore, the rotatable shearing member is rotated by using the exposed portion of the syringe as a handle, which would furnish an amount of leverage unlikely sufficient to shear the hub of a syringe should shearing edges be provided for that purpose.

Certain prior destructor devices provided shearing mechanism operated by squeezing hand levers together, as exemplified by U.S. Pat. No. 4,255,996. However, the squeezing force required to shear a syringe in this manner is quite substantial with the result that older hospital personnel found it increasingly difficult, especially if a number of syringes are cut at one time. Moreover, such devices usually embody a pivoted scissor-like design and the wearing and loosening of the pivot as well as dulling of the blades shortens the useful life of the device.

Further, such devices require opening to empty the cut-off parts, and while opened the contents are frequently spilled into a hospital environment where they are an obvious hazard by accidental transmission of dangerous diseases such as hepatitis.

DISCLOSURE OF THE INVENTION

The present invention is designed to overcome the aforesaid difficulties, and provides for shearing both the needle and the syringe in a single stroke with minimal effort, and for collecting and disposing of the severed parts in a sealed receptacle.

There are certain other so-called "sharps" including cartridge-needle units, blood collecting needles, spinal needles and various types of catheters which are not adapted to have both the cannula and associated hub or cartridge severed because the metal hub of certain units would damage the hub cutting edge, and the glass tube of certain other units would be smashed by the hub cutting edge creating a number of glass particles not desirable in the sterile environment of a health care facility.

The present invention also provides a separate orifice designed to receive and cut only the blood collecting or spinal needles or catheters without subjecting associated hubs or cartridges to cutting edges with undesirable results.

It is therefore a general object of the present invention to provide an improved destructor adapted selectively to destroy combination needle and syringe units in a single stroke, and to destroy only the needle of other sharps having metal hubs and/or glass cartridges.

Another object is to provide an improved needle and syringe destructor having a rotary die set having cutting edges for severing selectively the needle and syringe of certain units and the needle or cannula only of other units.

Another object is to provide an improved destructor adapted for collecting and storing the severed parts in a locked and inaccessible receptacle.

A further object is to provide improved means for automatically closing and locking the collecting receptacle on withdrawal from the destructor.

BRIEF DESCRIPTION OF THE DRAWINGS

FIG. 13 is a plan view of the receiving receptacle within the housing (shown in phantom) with the sliding closure for the receiving opening in open position.

FIG. 14 is partial plan view showing the sliding closure in closed position.

PREFERRED EMBODIMENT OF THE INVENTION

Figure 1:
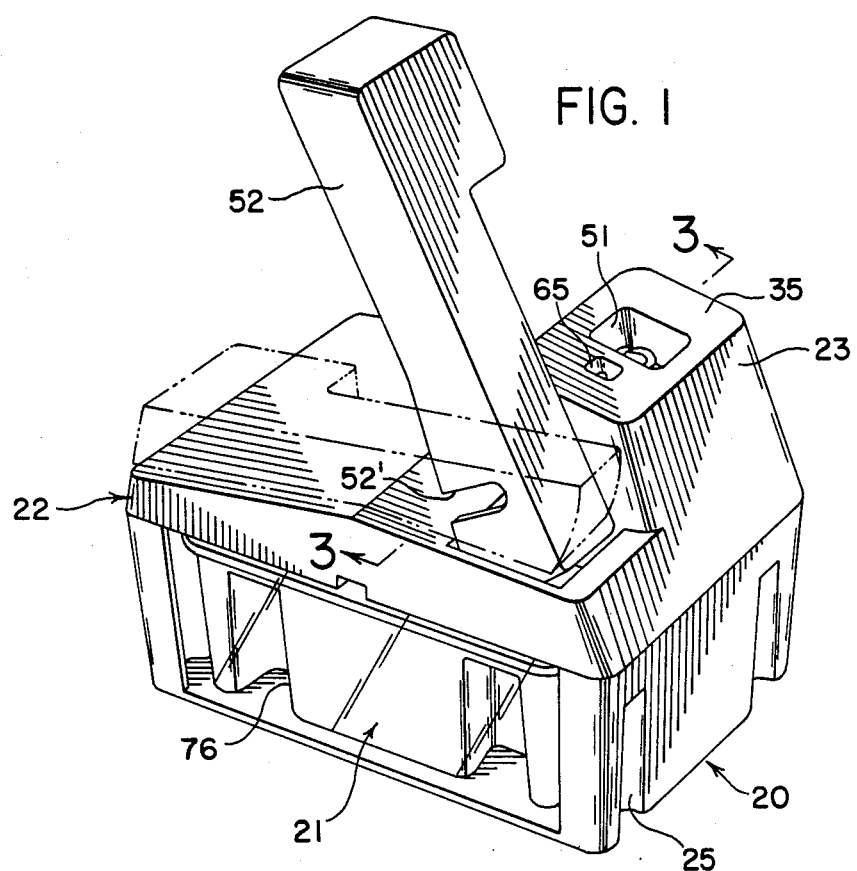
FIG. 1 is a perspective view of the improved needle and syringe destructor.
Figure 2:
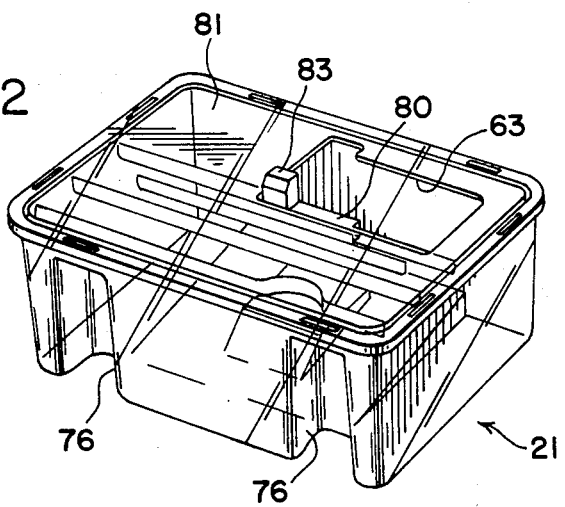
FIG. 2 is a perspective view of the receptacle for receiving severed parts.
Figure 4:
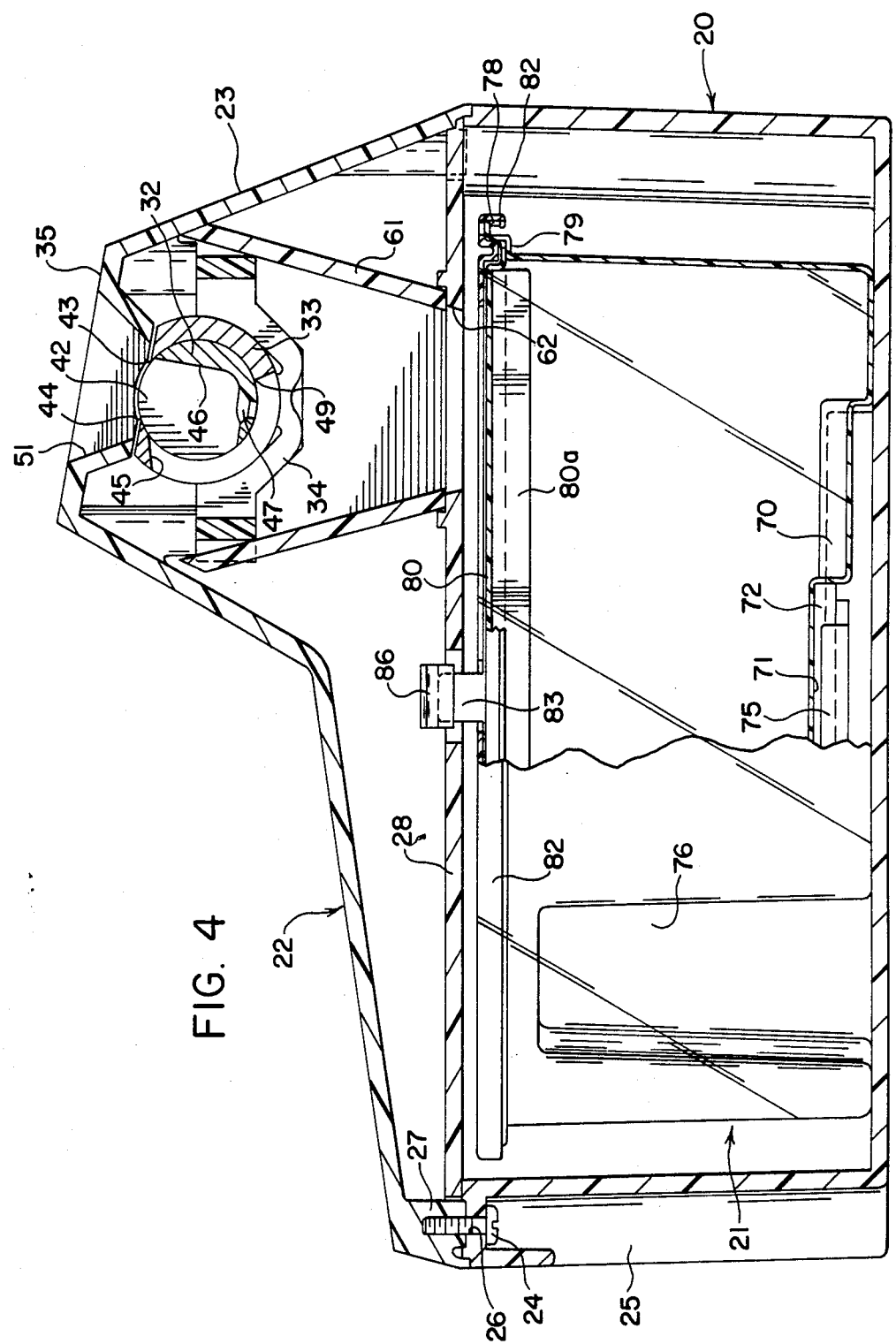
FIG. 4 is a sectional view on line 4—4 of FIG. 3.
Figure 7:
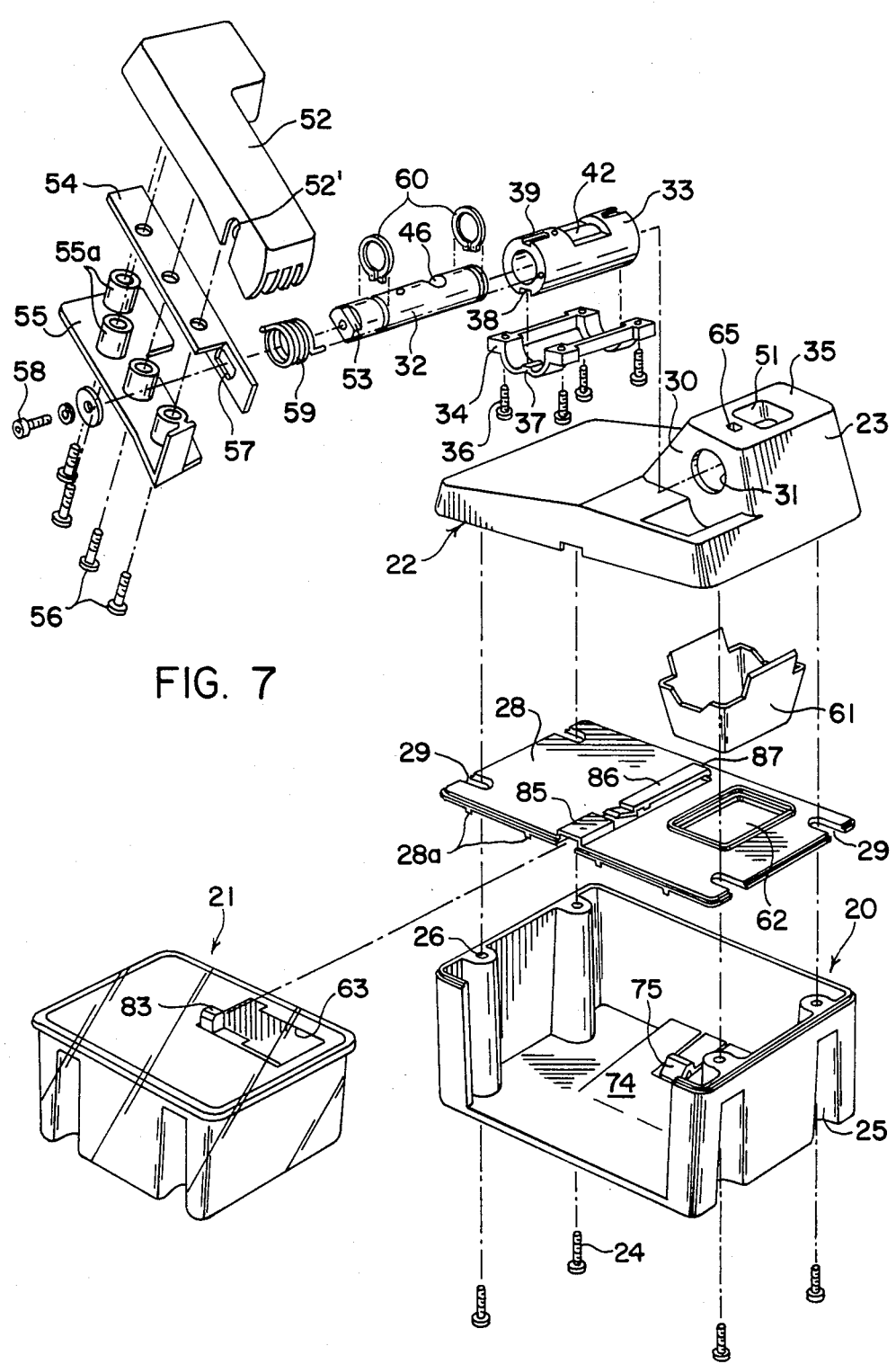
FIG. 7 is an exploded perspective view showing the relationship of the parts of the destructor.
Figure 8:
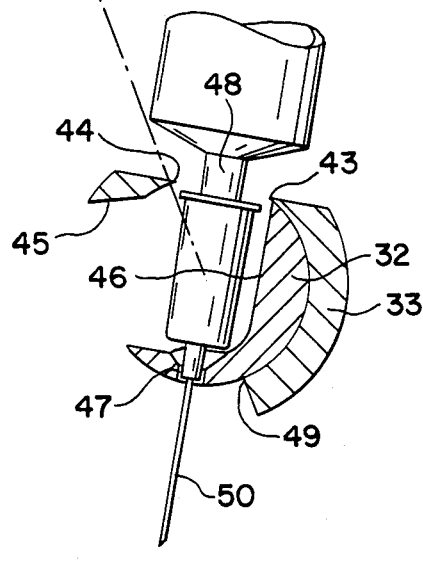
FIGS. 8–11 are enlarged schematic views showing the successive positions of the cutting dies during the operation of severing the needle and the hub of the syringe.
Figure 9:
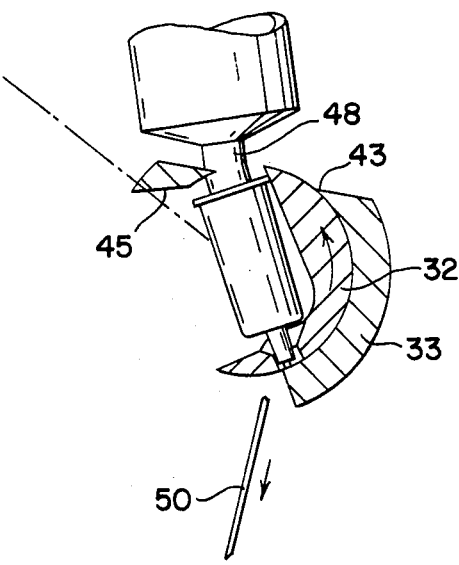
Figure 10:
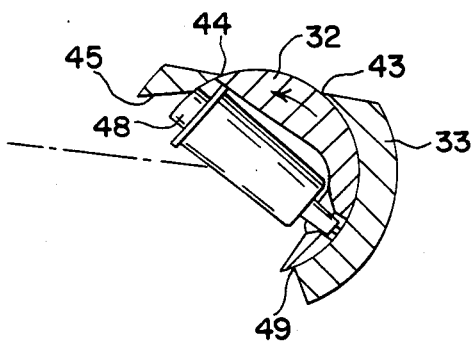
Figure 11:
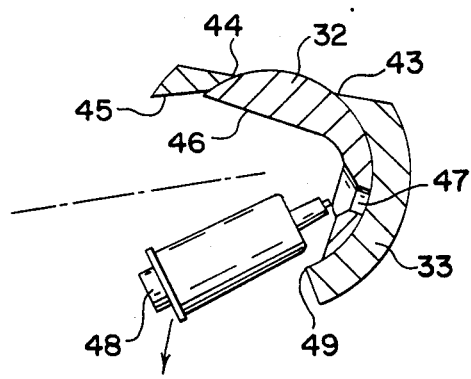

Referring to FIGS. 1, 2 and 7 of the drawings the outer housing consists of a base indicated generally at 20, with one side open to slidably receive the receptacle indicated generally at 21 in FIG. 2, and an upper closure body indicated generally at 22 having a raised portion 23 in which the cutting die set is mounted. The base housing 20 is secured to the upper body 22 by screws 24 inserted upwardly into the recesses 25 and through holes 26 and screwed into bosses 27 in the body (FIG. 4). An internal cover 28 is interposed between the upper body and the base housing and is provided with notches 29 at opposite edges through which the screws pass to secure the cover 28 in place. The base housing, upper body and receptacle and associated parts are preferably molded of suitable plastic materials, such as polycarbonate and polypropylene.

Figure 6:
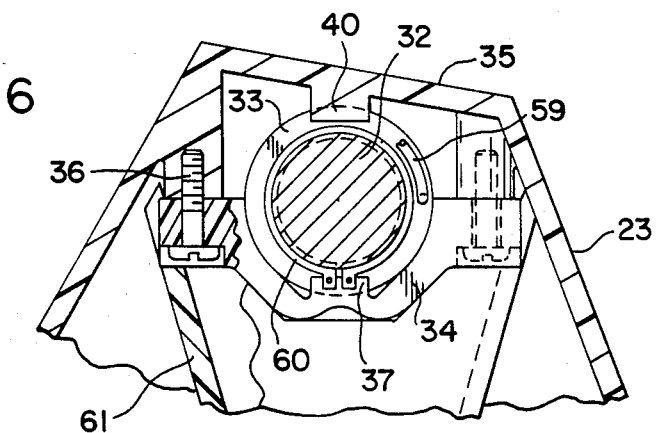
FIG. 6 is a partial sectional view on line 6—6 of FIG. 3.

The raised portion or dome 23 has a vertical wall 30 at its inner end provided with a circular opening 31 through which the cutting die set is inserted. The die set comprises an inner cylindrical core 32 rotatable within a hollow outer cylindrical sleeve 33 which is mounted in a bracket 34 secured to the upper wall 35 of dome 23 by screws 36. The bracket 34 has key portions 37 fitting in bottom grooves 38 in die sleeve 33 to non-rotatively secure the sleeve. The die sleeve also has top grooves 39 interfitting key projections 40 on the underside of top wall 35 (FIG. 6).

As shown in FIGS. 3, 4 and 7-11, the outer die sleeve has a rectangular opening 42 in its upper wall bounded by opposed edges 43 and 44. Below the edge 44 is a slot 45 communicating with opening 42 and extending substantially half way around the circumference of die sleeve 33. The die core 32 has a slot 46 which in the position of FIGS. 4 and 8 registers with the slot 42, except for a funnel-shaped opening 47 in the bottom wall of the slot 46 adapted to receive the needle or cannula of a syringe, but not large enough for the hub of the syringe to pass therethrough. The top edge of the slot 46 at 43 is a shearing edge for the syringe hub 48 and the bottom edge 49 of slot 45 is a shearing edge for the cannula 50. The top wall 35 of the dome 23 has a funnel-shaped opening 51 for guiding the needle end of a syringe into the opening 42 in the die sleeve.

The handle 52 is secured to the flatted end 53 of the die core for severing the cannula 50 and syringe hub 48 in the manner shown in FIGS. 8-11 by rotating the die core 32 in a counterclockwise direction. The positions of the center line of handle 52 are indicated in dot-dash lines C in FIGS. 8-11. The handle has a stiffener angle 54 (FIG. 7) secured to its underside by a retainer bar 55 having tubular bosses 55a through which screws 56 are inserted, and the angle 54 has a flatted opening 57 for fitting the flatted end 53 of the die core. The angle 54 is secured on the end 53 by screw 58 and a torsion spring 59 encircles the end portion of the die core for returning the handle to upright position after a counterclockwise stroke. A notch 52' in the side wall of handle 52 gives access to the screw 58. One end of the spring 59 is secured in the angle 54 and the other end is secured in the periphery of the die sleeve 33. The die core is held within the die sleeve 33 by snap ring washers 60.

Figure 3:
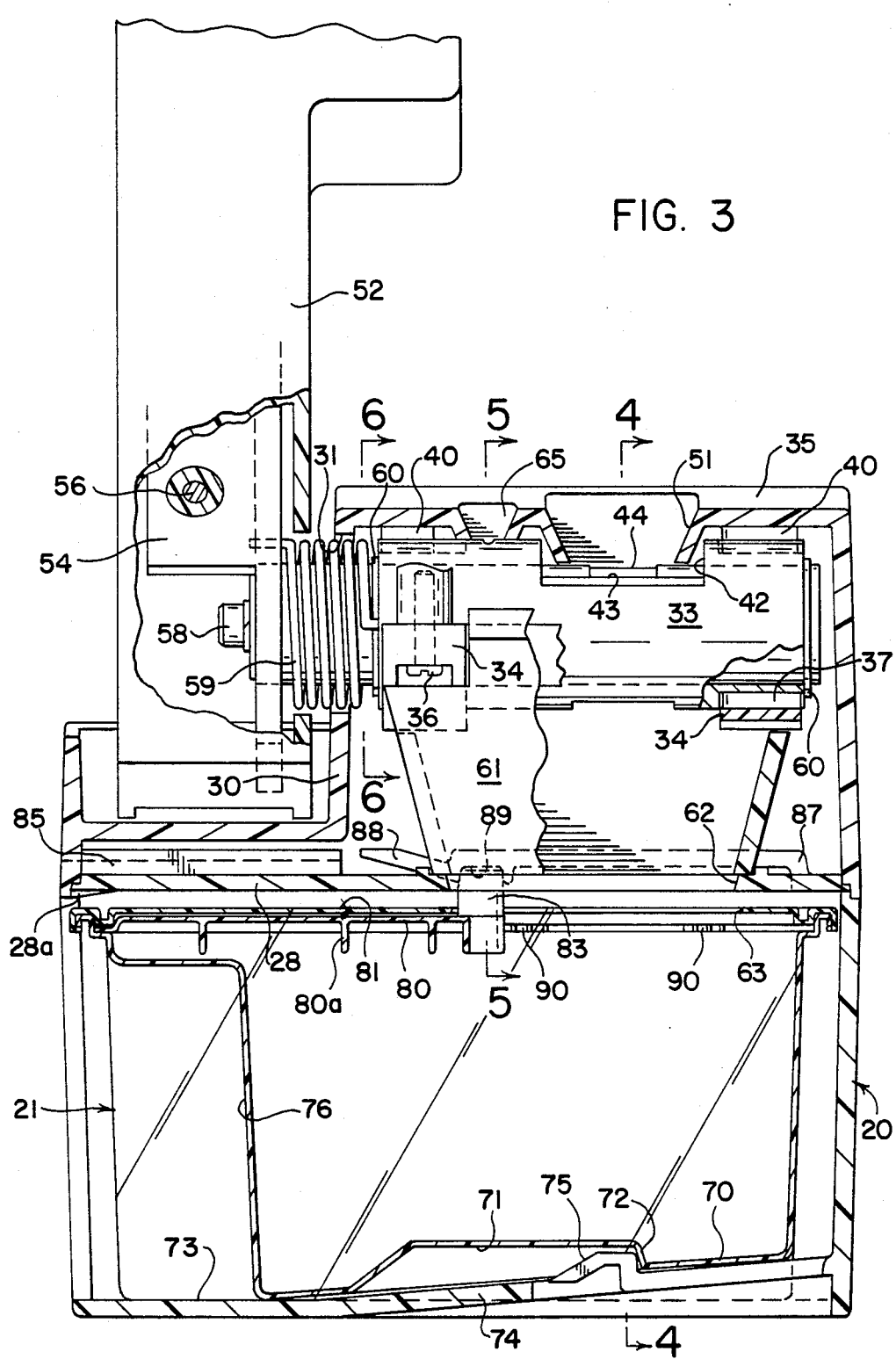
FIG. 3 is a cross-sectional view of the assembled destructor as on line 3—3 of FIG. 1, with parts broken away.

Referring to FIGS. 3, 4 and 7, a funnel 61 having a rectangular base is positioned around the bracket 34 and rests on the cover 28 around the edge of a rectangular opening 62 therein. The opening 62 is adapted to register with a rectangular opening 63 in receptacle 21 when it is positioned within the housing 20 as shown in FIG. 1. Thus, when the cannula 50 and the syringe hub 48 are severed as shown in FIGS. 8-11, both severed parts drop into the receptacle 21.

Figure 5:
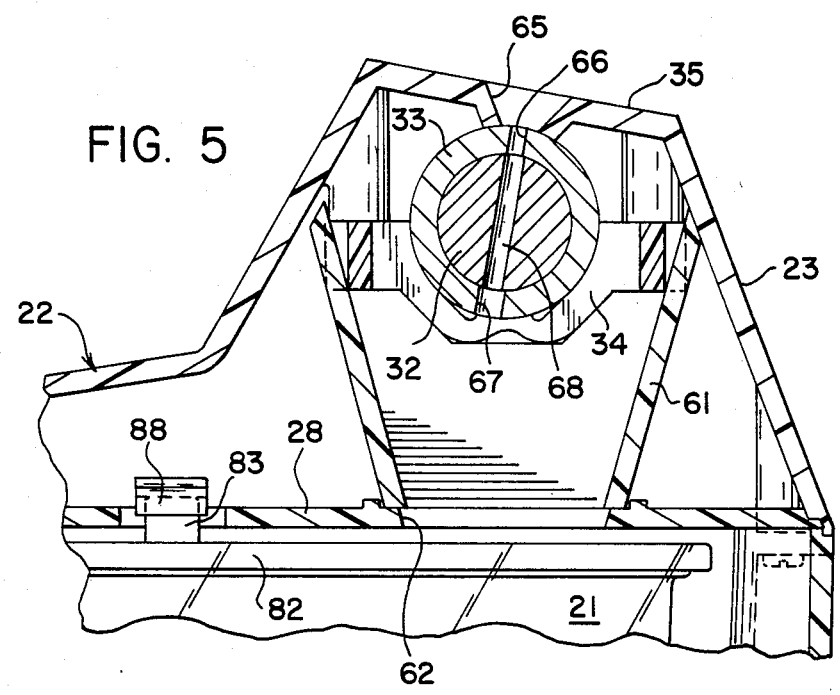
FIG. 5 is a partial sectional view on line 5—5 of FIG. 3.

For certain units or sharps where it may be desirable to destruct a needle only, there is provided a separate small opening 65 in top wall 35 for receiving the needle. As shown in FIG. 5, when handle 52 is in upright position, the opening 65 is aligned with openings 66 and 67 in the top and bottom of die sleeve 33, and also with a through opening 68 in die core 32. Accordingly, when the die core 32 is rotated counterclockwise, the point of the needle is severed and drops through the openings 68 and 67 and thence into receptacle 21.

Referring to FIGS. 1-4, 7, 12 and 15, the receptacle 21 has an inclined bottom wall portion 70 with an upwardly directed recess 71 forming a transverse shoulder 72 at its rear edge. The bottom wall 73 of the base housing 20 has a similarly inclined bottom portion 74 with a resilient tongue 75 therein adapted to enter the recess 71 when the receptacle 21 is slid into the base housing 20. Thus, the receptacle is resiliently held within the base housing, but may be removed by a positive pull on the receptacle for which purpose hand hold grooves 76 are provided in the front wall of receptacle 21.

Figure 12:
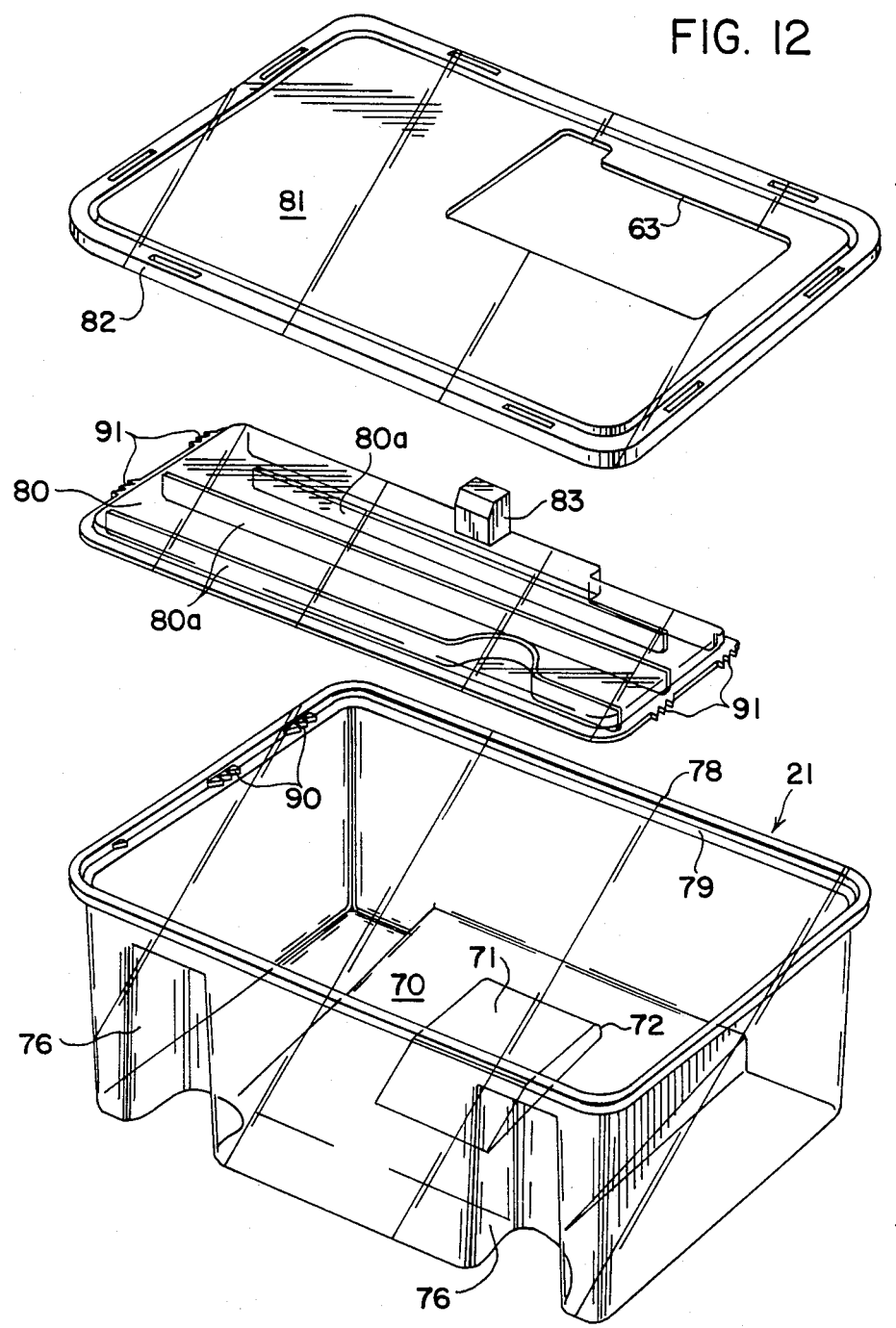
FIG. 12 is an exploded perspective of the receiving receptacle for severed parts.
Figure 16:
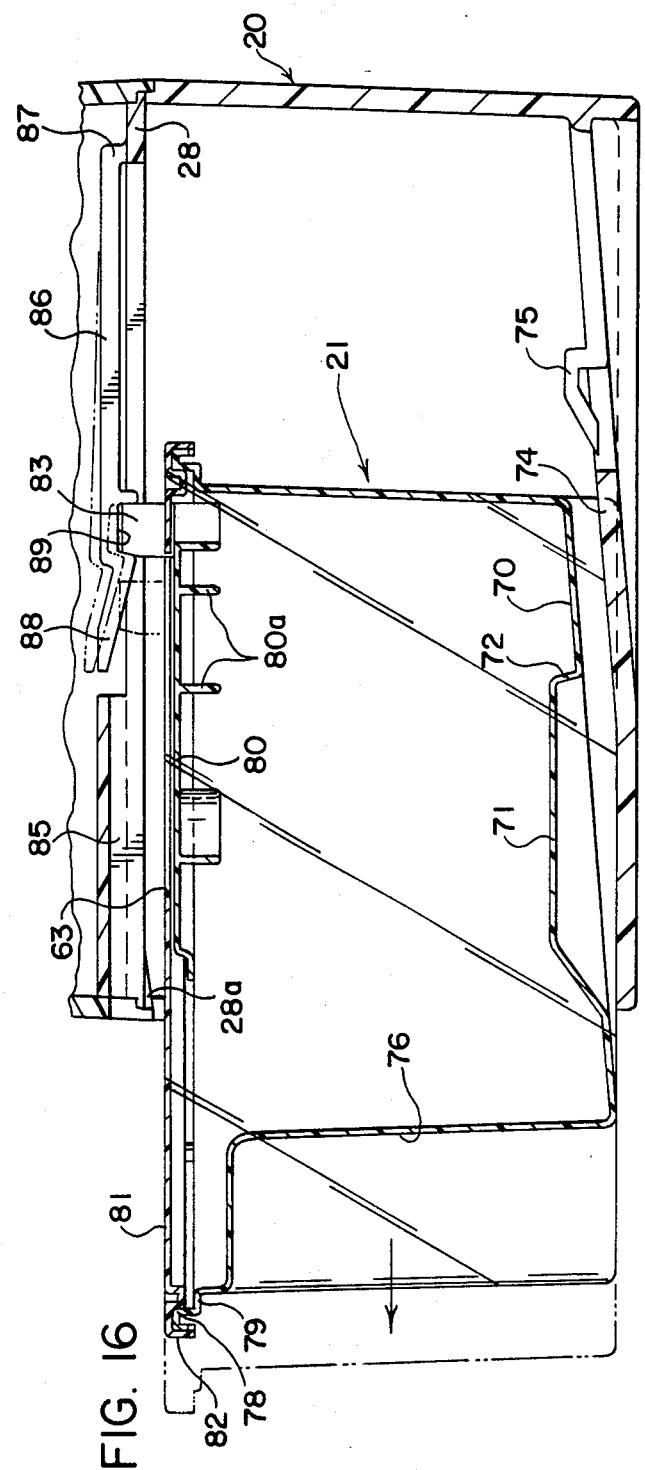
FIG. 16 is an enlarged partial sectional view on line 16—16 of FIG. 14.

Referring to FIGS. 12 and 16, the receptacle 21 has an upper rim 78 with an inner ledge 79, and a door 80 is adapted to rest on the ledge within the rim and below the cover 81 which has a downturned peripheral flange 82 adapted to fit over the rim 78 of the base housing. The door 80 has an upwardly projecting lug 83 which extends through the front corner of opening 63 when the door is over the front portion of receptacle 21 to place the opening 63 in open position, as seen in FIG. 13. Preferably, the under surface of the door 80 is provided with strengthening ribs 80a.

Figure 15:
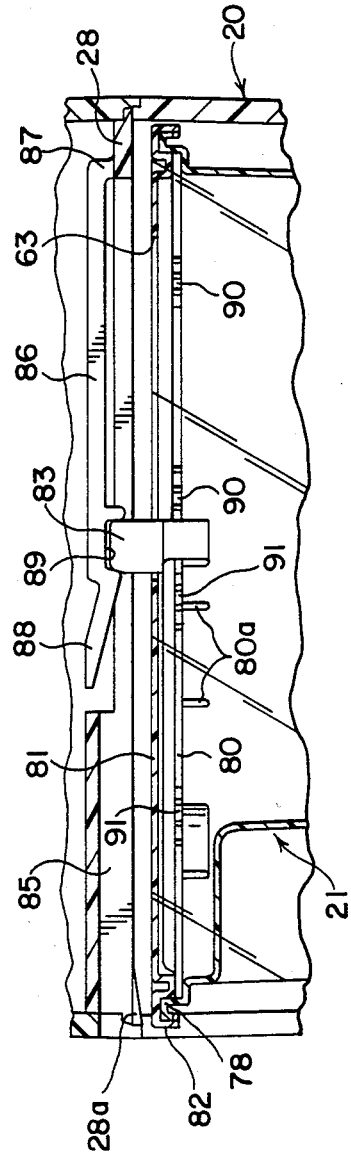
FIG. 15 is an enlarged partial sectional view on line 15—15 of FIG. 13.

The cover 28 which is secured to the top of base housing 20 under the upper body 22 has an upstanding channel portion 85 extending from the front toward the rear, in which the lug 83 is adapted to slide when the receptacle is inserted with the door 80 in open position of FIG. 13. An elongated strip 86 extends to the rear of said channel in alignment therewith and is connected at its rear end to the cover 28 by a living hinge 87. The front end of the strip has an inclined tongue 88 terminating at a recess 89 adapted to receive the lug 83 when the receptacle 21 is pushed into the base housing, causing the lug 83 to lift the tongue 88 and enter the recess 89, as seen in FIG. 15.

As shown in FIG. 16 when it is desired to withdraw the receptacle 21 a relatively strong pull on the receptacle will cause the bottom shoulder 72 to ride over the resilient tongue 75, and because of the engagement of lug 83 in recess 89 the door 80 will be held stationary and the relative movement of the receptacle will bring the door to the closed position of FIGS. 14 and 16. A continuing pull on the receptacle will cause the lug 83 to lift the tongue 88 of strip 86, thereby releasing the receptacle for complete withdrawal. As shown in FIGS. 3, 7, 15 and 16, the outer edge of cover 28 is provided on its underside with laterally spread ramps 28a which aid in guiding the receptacle 21 out of the base 20.

As shown in FIGS. 12-15, the laterally opposite inner edges of the upper rim 78 of receptacle 21 are provided with sets of ratchet teeth or serrations 90, and the laterally opposite edges of the door 80 have cooperating sets of ratchet teeth 91 such that the door may move from the open position of FIG. 13 to the closed position of FIG. 14, but is locked against movement from closed to open position. Accordingly, when the receptacle is withdrawn from the base housing, the contaminated severed needles and syringe parts are not accessible and the closed receptacle is thrown away and replaced.

The improved construction provides a destructor for syringes and/or cannulas which has a powerful leverage for severing both the cannula and the hub of the syringe of certain units in one stroke of rotary movement of a handle lever and provides a separate receiving orifice and cutting edge for destroying the needle only of other sharps.

The action of pressing down on the handle 52 to shear the cannula and the syringe is much easier than squeezing two hand levers together in a scissors-like device. Moreover, the novel die set cannot become loose by wear as is the case with the pivot in such prior squeezable hand lever devices, and is self-guiding for inserting a syringe to be severed.

The improved disposable receptacle 21 with its self-closing cover prevents spillage when the unit is emptied and its translucent walls allow viewing the level of the enclosed severed parts without opening the receptacle.

We claim:

1. A needle and syringe destructor comprising a base housing and an upper closure body therefor, rotary die means mounted in said closure body for severing needles and syringes, a receptacle slidable into and out of said base housing, guide means in said closure body for directing the severed parts into said receptacle, a cover for said receptacle, and means for automatically closing said cover as said receptacle is withdrawn from said base housing.

2. A needle and syringe destructor as defined in claim 1, wherein a handle lever is operatively connected to said rotary die means for severing a needle and attached syringe in one stroke.

3. A needle and syringe destructor as defined in claim 2, wherein said die means is provided with separate severing means for needles only.

4. A needle and syringe destructor as defined in claim 3, wherein said die means comprises an outer die sleeve fixedly mounted in said closure body and an inner die core coaxially rotatable in said die sleeve, said die means adapted to sever both a needle and an attached syringe in one stroke.

5. A needle and syringe destructor as defined in claim 1, wherein cooperating means on said cover and receptacle automatically locks the cover in closed position on the receptacle as it is withdrawn.

6. A needle and syringe destructor as defined in claim 5, wherein a handle lever is operatively connected to said rotary die means for severing a needle and attached syringe in one stroke.

7. A needle and syringe destructor as defined in claim 6, wherein said die means is provided with separate severing means for needles only.

8. A needle and syringe destructor as defined in claim 7, wherein said die means comprises an outer die sleeve fixedly mounted in said closure body and an inner die core coaxially rotatable in said die sleeve, said die means adapted to sever both a needle and an attached syringe in one stroke.

9. A needle and syringe destructor as defined in claim 1, wherein said die means is provided with separate severing means for needles only.

10. A needle and syringe destructor as defined in claim 9, wherein said die means comprises an outer die sleeve fixedly mounted in said closure body and an inner die core coaxially rotatable in said die sleeve, said die means adapted to sever both a needle and an attached syringe in one stroke.

11. A needle and syringe destructor as defined in claim 1, wherein said die means comprises an outer die sleeve fixedly mounted in said closure body and an inner die core coaxially rotatable in said die sleeve, said die means adapted to sever both a needle and an attached syringe in one stroke.

* * * * *